(12) United States Patent
Sreedharala (10) Patent No.: US 11,110,077 B2
(45) Date of Patent: Sep. 7, 2021

(54) APREMILAST PHARMACEUTICAL COMPOSITIONS

(71) Applicant: SARUDBHAVA FORMULATIONS PRIVATE LIMITED, Hyderabad (IN)

(72) Inventor: Venkata Nookaraju Sreedharala, Hyderabad (IN)

(73) Assignee: SARUDBHAVA FORMULATIONS PRIVATE LIMITED, Hyderabad (IN)

( * ) Notice: Subject to any disclaimer, the term of this patent is extended or adjusted under 35 U.S.C. 154(b) by 0 days.

(21) Appl. No.: 16/088,801

(22) PCT Filed: Sep. 30, 2016

(86) PCT No.: PCT/IN2016/000237
§ 371 (c)(1),
(2) Date: Sep. 26, 2018

(87) PCT Pub. No.: WO2017/168433
PCT Pub. Date: Oct. 5, 2017

(65) Prior Publication Data
US 2019/0046505 A1    Feb. 14, 2019

(30) Foreign Application Priority Data

Mar. 30, 2016  (IN) .............................. 201641011015
Sep. 30, 2016  (WO) ................. PCT/IN2016/000237

(51) Int. Cl.
| | | |
|---|---|---|
| *A61K 31/4035* | (2006.01) | |
| *A61K 9/00* | (2006.01) | |
| *A61K 9/06* | (2006.01) | |
| *A61K 47/20* | (2006.01) | |
| *A61P 17/06* | (2006.01) | |

(52) U.S. Cl.
CPC ........ *A61K 31/4035* (2013.01); *A61K 9/0014* (2013.01); *A61K 9/06* (2013.01); *A61K 47/20* (2013.01); *A61P 17/06* (2018.01)

(58) Field of Classification Search
CPC ...... A61K 31/4035; A61K 9/06; A61K 47/20; A61K 9/0014; A61P 17/06
See application file for complete search history.

(56) References Cited

U.S. PATENT DOCUMENTS

| | | | | |
|---|---|---|---|---|
| 3,711,602 | A | * | 1/1973 | Herschler ............ A61K 9/0014 424/45 |
| 9,765,026 | B2 | * | 9/2017 | Fang .................... C07D 209/50 |
| 2006/0183787 | A1 | * | 8/2006 | Muller ............... A61K 31/4035 514/417 |
| 2015/0231262 | A1 | * | 8/2015 | Kisak .................... A61K 47/38 514/567 |

FOREIGN PATENT DOCUMENTS

| | | | | |
|---|---|---|---|---|
| CN | 106924174 A | * | 7/2017 | |
| WO | WO-2012121988 A2 | * | 9/2012 | ........... A61K 9/0014 |
| WO | WO-2016198469 A1 | * | 12/2016 | ............. A61K 47/10 |

OTHER PUBLICATIONS

CN-106924174—A machine translation (Year: 2017).*
Drugs in the pipeline hold promise for atopic dermatitis Publish date: Aug. 31, 2016 By Doug Brunk (Year: 2016).*

* cited by examiner

*Primary Examiner* — Sarah Pihonak
*Assistant Examiner* — Jason Deck
(74) *Attorney, Agent, or Firm* — Schmeiser, Olsen & Watts, LLP (57) ABSTRACT

The present invention relates to topical pharmaceutical compositions of apremilast used for the treatment of psoriasis and/or psoriatic arthritis. It further relates to processes of preparation of the compositions and the method of use for these compositions.

13 Claims, 4 Drawing Sheets

Extent of Psoriasis Type Symptoms shown with the Application of Imiquimod Cream

Figure – 5

Extent of decrease of Psoriasis by the application of 5mg of Test

Figure – 6

Extent of decrease of Psoriasis by the application of 50mg of Test

Figure – 7

Extent of decrease of Psoriasis by the application of 100mg of Test

Figure – 8

Extent of decrease of Psoriasis by administration of oral suspension

APREMILAST PHARMACEUTICAL COMPOSITIONS

CROSS-REFERENCE TO RELATED APPLICATIONS

This application claims priority to PCT Application No. PCT/IN2016/000237, having a filing date of Sep. 30, 2016, which is based off of IN Application No. 201641011015, having a filing date of Mar. 30, 2016, the entire contents both of which are hereby incorporated by reference.

FIELD OF THE INVENTION

The present invention relates to topical pharmaceutical compositions for the treatment of psoriasis and/or psoriatic arthritis.

BACKGROUND OF THE INVENTION

Apremilast is a phosphodiesterase4 (PDE4) inhibitor. Apremilast is known chemically as N-[2-[(1S)-1-(3-ethoxy-4-methoxyphenyl)-2-(methylsulfonyl)ethyl]-2,3-dihydro-1,3-dioxo-1H-isoin-dol-4-yl]acetamide, having chemical structure as given below:

Apremilast

Apremilast is at present available only as an oral formulation, marketed by Celgene Corp, under the trade name of OTEZLA®. OTEZLA® tablets are supplied in 10, 20, and 30 mg strengths for oral administration. OTEZLA® tablets are indicated (1) for the treatment of patients with active psoriatic arthritis and (2) for the treatment of patients with moderate to severe psoriasis who are candidates for phototherapy or systemic therapy.

Psoriasis is a chronic, non-contagious skin disorder that appears in many different forms and can affect any part of the body. The most common type of psoriasis is plaque psoriasis, occurring in 80% of people suffering from the disease. Plaque psoriasis is characterized by red patches and lesions that are covered by a build up of skin cells that are often called scales, and most commonly seen on the elbows, knees, scalp and back. Psoriasis is classified as mild, moderate, or severe, depending on the percentage of body surface involved and severity of the disease.

According to the National Institutes of Health, psoriasis is one of the most common human skin disorders, affecting greater than 3% of the United States population, or more than 5 million adults, of which greater than 1.5 million are considered to have a moderate to severe form of the disease. Although psoriasis is not fatal, it negatively impacts quality of life to a degree similar to heart disease and arthritis (Rapp et al. 1999). In addition, 10-30% of patients with psoriasis also develop a form of arthritis—psoriatic arthritis, which damages the bone and connective tissue around the joints. Furthermore, inflammatory mediators associated with psoriasis may increase the risk of obesity, diabetes, thrombosis, and atherosclerosis (Davidovici et al. 2010).

Though, apremilast is available as an effective oral therapy for psoriasis; an oral tablet composition is less suitable for patients who have difficulty in swallowing or whose gastro intestinal side effects are not reduced even after suggested oral dose titration. Thus, there is need for an effective pharmaceutical composition of apremilast suitable for topical administration that overcomes the problems associated with oral compositions.

OBJECT OF THE INVENTION

It is therefore an object of the invention to provide a safe and effective pharmaceutical composition comprising apremilast, suitable for topical administration.

Another object of the present invention is to provide a topical pharmaceutical composition comprising apremilast, effective in the treatment of psoriasis.

Yet another object of the present invention is to provide a simple method for preparation of a topical pharmaceutical composition comprising apremilast.

SUMMARY OF THE INVENTION

The inventors developed a novel composition designed for topical application comprising apremilast as the active ingredient, and surprisingly discovered that the composition effectually treated psoriasis without producing any of the negative side effects associated with oral administration as described in the prior art. Thus, the presently disclosed method provides a means of treating psoriasis that is cosmetically acceptable, effective, and easy to apply.

Thus, in one aspect the present invention provides a pharmaceutical composition of apremilast suitable for topical administration having desired pharmacological activity and fewer side effects.

In another aspect, the present invention is directed to a topical composition comprising a therapeutically effective amount of apremilast and a pharmaceutically acceptable topical carrier.

In yet another aspect, the present invention is directed to methods of treating psoriasis by topical application to an affected epidermal area of a subject a topical dosage form comprising apremilast; and continuing the administration until symptoms of psoriasis are abated.

In another aspect, the present invention sets forth a safe and commercially viable process for preparation of a topical composition of apremilast that is sufficiently stable to provide an acceptable shelf life.

DETAILED DESCRIPTION OF THE INVENTION

It has been surprisingly been found that pharmaceutical compositions of apremilast in the form of topical formulations provide desired pharmacological actions and fewer side effects.

Accordingly, the present invention is directed to topical compositions comprising apremilast as the primary active agent and methods of use thereof for treating psoriasis. Specifically, the disclosed topical composition may be a cream, lotion, spray, oil, ointment, paste, dressing, solution, gel or other types of compositions that lends itself to topical application.

In one embodiment, the invention is directed to a topical composition for treating psoriasis comprising a therapeutically effective amount of apremilast and a pharmaceutically acceptable carrier.

A "therapeutically effective amount" is an amount necessary to palliate at least one symptom of psoriasis. For example, a therapeutically effective amount is sufficient to treat (i.e. alleviate or reduce) at least one of: itching/scratching, redness, inflammation, cracking, scaling, bleeding, etc. Preferably, the therapeutically effective amount of apremilast comprises between 0.5 to 15% by weight of the composition, more preferably 2 to 10%.

The term "pharmaceutically acceptable" means approved by a regulatory agency of the Federal or state government or listed in the U.S. Pharmacopeia or other generally recognized pharmacopeia for use in animals, and more particularly in humans.

The term "carrier" refers to a diluent, adjuvant, excipient, penetration enhancer, or vehicle with which an active ingredient is administered. Such pharmaceutical carriers can be liquids, such as water and oils, including those of petroleum, animal, vegetable or synthetic origin. Preferably, the pharmaceutically acceptable carrier comprises excipients commonly used in topically applied formulations (water, oil-based lotions, sprays, ointments, gels etc.).

As a non-limiting example, a pharmaceutically acceptable carrier may comprise water, glycerin, petrolatum, stearic acid, glycol stearate, dimethicone, isopropyl isostearate, tapioca starch, cetyl alcohol, glyceryl stearate, magnesium aluminum silicate, carbomer, ethylene brassylate, triethanolamine, disodium EDTA, phenoxyethanol, methyl paraben, propyl paraben, ethanol, bio-polymers (e.g., sodium hyaloronate), liposomes, nano- and micro-particulate carriers, and/or titanium dioxide. More preferably, the pharmaceutically acceptable carrier comprises dimethyl sulfoxide (DMSO), glycerol, propylene glycol, petrolatum water, and one or more pharmaceutically acceptable penetration enhancer (absorption promoter and/or accelerants).

In a preferred embodiment, the pharmaceutical composition is in the form of topical gel or cream or ointment or solution or spray comprising apremilast and dimethyl sulfoxide (DMSO); in the ratio of 1:100 to 100:1, preferably 1:10 to 10:1, more preferably 1:1.

Typically, the topical compositions of the invention comprise skin penetration enhancers, pharmaceutical surfactants and solubility enhancers, oil phase components, aqueous phase components, emulsifiers, moisturizers, antioxidants, vitamins, lubricants, preservatives, stabilizers and other ingredients.

Skin penetration enhancers reversibly decrease the barrier resistance of the skin, which increases the amount of apremilast absorbed. Preferably, skin penetration enhancers include, but are not limited to, sulfoxides (e.g. DMSO), azones (e.g. laurocapram), pyrrolidones (e.g., 2-pyrrolidone), alcohols and alkanols (e.g., ethanol, decanol, etc.), oleic acid (and derivatives thereof), glycols (e.g., propylene glycol), dimethylformamide (DMF), dimethylacetamide (DMAC), fatty alcohols (e.g., lauryl alcohol), fatty acid esters, fatty acids, fatty alcohol ethers (e.g., EO-2-oleyl ether), terpenes, and biologics (e.g., lecithin).

Pharmaceutical surfactants or solubility enhancers include, but are not limited to, lauryl alcohol, polyoxyethylene ether, polyoxyethylene glycerol monostearate, stearic acid ester oxygen poly hydrocarbon, vitamin E succinate polyethylene glycol ester, sorbitan esters, polyoxyethylene castor oil, polyoxyethylene hydrogenated castor oil, poloxamer, organic esters (e.g. ethylene acetate), and poly hill dinitrate 80 (i.e. Tween 80 or its mixture). In a preferred embodiment, the pharmaceutical surfactants or solubility enhancers include DMSO, polyvinylpyrrolidones, stearic acid hydrocarbon oxygen Poly (40) ester, lauryl alcohol polyoxyethylene (23) ether, vitamin E succinate polyethylene glycol ester, ethylene acetate, and polyoxyethylene (40) hydrogenated castor oil (and its mixtures, i.e. polyoxy (40) stearate). Still, in a more preferred embodiment the pharmaceutical surfactants or solubility enhancers include sodium lauryl sulphate and sorbitan esters.

Suitable oily phase may include, but are not limited to, glyceryl monoacetate, glycerol diacetate, glyceryl triacetate, stearic acid, soybean oil, corn oil, peanut oil, palmitic acid, palm oil, sunflower oil, olive oil, coconut oil, sesame oil, cotton seed oil, rapeseed oil, oleic acid, medium-chain triglycerides, single-decane triglyceride, animal fat (e.g., lanolin), mineral oils, paraffin, beeswax, petrolatum, hydrocarbons, vaseline, and mixtures thereof.

Aqueous phase components include, but are not limited to, de-ionized water, glycerol gelatin, cellulose derivatives (e.g., microcrystalline cellulose (Avicel PH 101)), and polyethylene glycol (PEG 300 to PEG 6000), and mixtures thereof.

Emulsifiers include, but are not limited to oleyl alcohol, polyoxyethylene oleyl ether, PEG-40 stearate, ceteareth-12, ceteareth-20, ceteareth-30, glyceryl stearate, PEG-100 stearate, methyl myristate, isopropyl myristate, Arlacel 165, glyceryl stearate, PEG-100 stearate, steareth-2 and steareth-20, dimethicone copolyol, Polysorbate 20 (Tween 20), cetyl esters wax, Polysorbate 40 (Tween 40), Polysorbate 60 (Tween 60), Polysorbate 80 (Tween 80), lauramide DEA, cocamide DEA, and cocamide MEA, Phospholipid PTC, alginate, carrageenan, Glucate DO, methylcellulose, polyvinyl alcohol, homopolymers of acrylic acid crosslinked with allyl sucrose or allyl pentaerythritol (Carbomer). Preferably, emulsifiers are selected from the group consisting of cetostearyl alcohol, stearic acid, magnesium stearate, sodium lauryl sulfate, triethanolamine, and magnesium aluminum silicate.

Moisturizers include, but are not limited to, glycerol, propylene glycol, and sorbitol.

Antioxidants include, but are not limited to, water soluble antioxidants, lipid-soluble antioxidants, vitamin C, vitamin C palmitate, propyl gallate, vitamin E (tocopherol), tert-butyl ether-hydroxybenzoate fennel, 2,6 di-tert-butyl-p-cresol, BHA, BHT, or mixtures of one or more antioxidants.

Lubricants include, but are not limited to, urea, magnesium stearate, sodium lauryl sulfate, polyethylene glycol, and silica gel powder.

Preservatives include, but are not limited to, chloro-m-cresol, citric acid, disodium edetate, ethoxylated alcohol, glycerin, 1,2,6-hexanetriol, methylparaben, parabens, potassium, sorbate, propyl gallate, propylene glycol, propyl paraben, sodium bisulfate, sodium citrate, butyl paraben, sodium metabisulfite, chlorocresol, sorbic acid, tannic acid, zinc stearate, butylated hydroxytoluene, butylated hydroxyanisole, benzoic acid, salicylic acid, propyl paraben, dichlorobenzyl alcohol, formaldehyde, alpha-tocopherol, sodium ascorbate, ascorbic acid, ascorbyl palmitate phenol, m-cresol, bisphenol, cetrimide, benzalkonium chloride, sorbic acid, phenoxyethanol, and benzoyl peroxide. Preferably, preservatives are selected from the group consisting of hydroxylethyl benzene, hydroxylmethyl benzene, phenoxyethanol, chlorocresol, propyl paraben, and methyl paraben.

In an embodiment of the invention, topical composition of present invention has excipients that help adjusting the pH of the composition. Topical pharmaceutical compositions of the invention have a pH in the physiological range of 1 to 8, preferably 2 to 7, more preferably 3 to 6.

Suitable pH adjusting agents include many pharmaceutically acceptable acids, bases and buffers. Suitable acids may include one or more of hydrochloric acid, phosphoric acid and lactic acid. Suitable bases may include one or more of diethanolamine, triethanolamine and sodium hydroxide. Suitable buffers may include phosphates, such as monobasic sodium phosphate, dibasic sodium phosphate, lactates and citrates.

Suitable stabilizers include, but not limited to, chelating agents, stearyl alcohols.

The compositions of the present invention may further comprise excipients to provide better feel to the skin and lower irritation to the skin. The compositions may further contain additional excipients that enhance the aesthetic properties of the composition like coloring and flavoring agents.

In another aspect, the present invention is directed to methods of treating psoriasis by topical application to an affected epidermal area of a subject a topical dosage form comprising apremilast; and continuing the administration until symptoms of psoriasis are abated.

Accordingly in another embodiment, the invention is directed to a method of treating psoriasis comprising the steps of topically applying a composition comprising apremilast within a pharmaceutically acceptable carrier to an affected epidermal area of a subject suffering from psoriasis. As used herein, "affected epidermal area" refers to those patches of skin that exhibit common indicators of psoriasis including inflammation, erythema, hyperproliferation, cracking, scaling, and bleeding.

Furthermore, the method is directed to treating a type of psoriasis selected from the group consisting of plaque psoriasis, guttate psoriasis, inverse psoriasis, pustular psoriasis, and erythrodermic psoriasis. Most preferably, the method is directed to treating plaque psoriasis. Additionally, the subject suffering from psoriasis is an animal, preferably a mammal (e.g., pig, cow, horse, dog, cat, etc.), and most preferably the subject is a human.

In studies conducted thus far (see Example 8), no side effects have been observed. Thus, the methods disclosed herein represent a very desirable first- or second-line therapy for the treatment of psoriasis. Thus, in a preferred embodiment, the method is directed to the treatment of mild, moderate, or severe psoriasis and more preferably directed to the treatment of moderate or severe psoriasis.

In another aspect, the present invention sets forth a safe and commercially viable process for preparation of a topical composition of apremilast that is sufficiently stable to provide an acceptable shelf life.

Thus, in another embodiment, the present invention is directed to methods of preparation of pharmaceutical compositions of apremilast, suitable for topical administration, and effective in the treatment of psoriasis. The compositions of the present invention may be prepared through any of the processes and techniques known in the art. The inventor have designed different formulation procedures, and varieties of excipients of oil and aqueous phases, surfactants and solubility enhancers, and emulsifiers in order to develop stable, uniform, and cosmetically acceptable compositions.

The principles, preferred embodiments, and modes of operation of the present invention have been described in the foregoing specification. The invention which is intended to be protected herein, however, is not to be construed limited to the particular forms disclosed, since these are to be regarded as illustrative rather than restrictive. Variations and changes may be made by those skilled in the art, without departing from the spirit of the invention.

The following examples further illustrate the invention but should not be construed as in any way limiting its scope. In particular, the processing conditions are merely exemplary and can be readily varied by one of ordinary skill in the art.

EXAMPLES

Example 1: Topical Composition of Apremilast

| Component | % w/w |
| --- | --- |
| Apremilast | 5 |
| DMSO | 20 |
| PEG 400 | 25 |
| Propylene glycol | 12.5 |
| CARBOPOL® homoplymer | 1.5 |
| pH adjusting agents | QS pH 5 to 6 |
| Glycerin | QSAD 100 |

Manufacturing Process
  a) Approximately 100% of DMSO is weighed into a stainless steel vessel; propylene glycol and polyethylene glycol 400 are added and stirred with a propeller mixer.
  b) While stirring is continued, Ap01 is added to Step a) and mixed until dissolved.
  c) While stirring is continued, CARBOPOL® homopolymer is added slowly to Step b) and mixed vigorously at room temperature until a uniform and lump free dispersion is achieved.
  d) While stirring is continued, 80% of glycerin is added slowly to Step c) and the contents are mixed contents at room temperature until a uniform dispersion is achieved.
  e) While stirring is continued, sufficient pH adjusting agent is added to the mixture to achieve a pH of 5.0 to 6.0.
  f) The remaining glycerin is added and mixed until uniform dispersion is achieved.

g) The Dispersion is transferred to a storage vessel and filled.

Example 2: Topical Composition of Apremilast

| Component | % w/w |
|---|---|
| Apremilast | 0.5 |
| DMSO | 30 |
| PEG 400 | 5 |
| Propylene glycol | 13.3 |
| CARBOPOL ® homoplymer | 1.2 |
| pH adjusting agents | QS pH 5 to 6 |
| Glycerin | QSAD 100 |

Manufacturing Process
 a) Approximately 100% of DMSO is weighed into a stainless steel vessel; propylene glycol and polyethylene glycol 400 are added and stirred with a propeller mixer.
 b) While stirring is continued, Ap01 is added to Step a) and mixed until dissolved.
 c) While stirring is continued, CARBOPOL® homopolymer is added slowly to Step b) and mixed vigorously at room temperature until a uniform and lump free dispersion is achieved.
 d) While stirring is continued, 80% of glycerin is added slowly to Step c) and the contents are mixed contents at room temperature until a uniform dispersion is achieved.
 e) While stirring is continued, sufficient pH adjusting agent is added to the mixture to achieve a pH of 5.0 to 6.0.
 f) The remaining glycerin is added and mixed until uniform dispersion is achieved.
 g) The Dispersion is transferred to a storage vessel and filled.

Example 3: Topical Composition of Apremilast

| Component | % w/w |
|---|---|
| Apremilast | 0.5 |
| White Soft Paraffin | 90 |
| Liquid Paraffin | 7 |
| Sorbitan sesquioleate | 0.5 |
| Menthol | 1 |
| DMSO | 1 |

Manufacturing Process:
 a) White soft paraffin and sorbitan sesquioleate are added into a melting vessel and the contents are melted at 75° C.
 b) The mixture of Step (a) are transferred to Becomix and the contents are mixed at 10 rpm and cooled to 50° C.
 c) Ap01 is dissolved in DMSO in a separate vessel. The solution is dispersed in liquid paraffin maintained at 60° C. using a water bath, and the contents are homogenized using a homogenizer.
 d) With continuous stirring, Step c) to Step b) and mixed vigorously at room temperature until a uniform dispersion is achieved.
 e) The dispersion is homogenized under vacuum at 0.4-0.6 bar at 10 rpm.
 f) The Dispersion is transferred to a storage vessel and filled.

Example 4: Topical Composition of Apremilast

| Component | % w/w |
|---|---|
| Apremilast | 0.5 |
| Oleyl Alcohol | 10 |
| White soft Paraffin | 84.7 |
| Hard Paraffin | 0.3 |
| Microcrystalline wax | 3.5 |
| DMSO | 1 |

Manufacturing Process:
 a) White soft paraffin and microcrystalline wax are added into a melting vessel and melted by heating to 70° C.
 b) Mixture is transferred to Becomix, and maintained at 40° C.-45° C.
 c) With continuous stirring, oleyl alcohol is added to the base obtained in Step a) and maintained at 40° C.-45° C.
 d) Ap01 is dissolved in DMSO and add to the melt obtained in Step b), and homogenize for 5 minutes.
 e) The product of Step (d) is allowed to cool to 30° C. and transferred to storage vessel and filled.

Example 5: Topical Composition of Apremilast

| Component | % w/w |
|---|---|
| Apremilast | 0.5 |
| Methyl Paraben | 0.025 |
| Propyl Paraben | 0.015 |
| Sodium Lauryl Sulphate | 1 |
| DMSO | 1 |
| Propylene Glycol | 12 |
| Stearyl alcohol | 25 |
| White Petrolatum | 25 |
| Water | 36 |

Manufacturing Process:
 a) Stearyl alcohol and white petrolatum are added on a steam bath into a melting vessel and heated to about 75° C.
 b) Ap01 is dissolved in DMSO; and the other ingredients in purified water; and warmed to about 75° C.
 c) All ingredients are mixed together and stirred until the mixture congeals.
 d) The mixture is transferred to a storage vessel and filled.

Example 6: Topical Composition of Apremilast

| Component | % w/w |
|---|---|
| Apremilast | 0.5 |
| White wax | 12 |
| Cetyl esters wax | 12 |
| Mineral Oil | 40 |
| DMSO | 15 |
| Sodium Borate | 0.5 |
| Water | 20 |

Manufacturing Process:
 a) White wax and cetyl ester wax are added into a melting vessel and the components are melted at 70° C.

b) Mineral oil is added to the mix obtained in Step a) and further mixed until uniform mixture is obtained.
c) Ap01 is dissolved in DMSO and added to the mix obtained in Step b).
d) Water and sodium borate is added to the mix of Step c).
e) While continuous mixing, water phase is slowly added to the oil phase.
f) The mixture is transferred to a storage vessel and filled.

Example 7: Topical Composition of Apremilast

| Component | % w/w |
| --- | --- |
| Apremilast | 0.5 |
| Propylene Glycol | 48.025 |
| Glyceryl Monostearate | 5 |
| Cetostearyl alcohol | 4 |
| White wax | 0.6 |
| Chlorocresol | 0.075 |
| Water | 40 |
| DMSO | 1 |

Manufacturing Process:
a) White wax, cetostearyl alcohol, and glyceryl monostearate are added into a melting vessel and mixed continuously while heating to 75° C. DMSO is added and mixed until uniform.
b) Ap01 is added to the mix obtained in Step a) and the temperature is maintained at 75° C.
c) Water and propylene glycol are added into a melting vessel and the contents are heated to 61-65° C.
d) Chloro cresol is added to the water phase and mixed until uniform mixture is obtained.
e) Water phase is slowly added to the oil phase with continuous stirring.
f) The mixture is transferred to a storage vessel and filled.

Example 8: Topical Composition of Apremilast

| Component | % w/w |
| --- | --- |
| Apremilast | 2.00 |
| Dimethyl Sulfoxide | 30.00 |
| CARBOPOL ® homoplymer | 1.20 |
| Glycerin | 66.70 |
| Methyl Paraben | 0.10 |

Manufacturing Process
a) Approximately 100% of DMSO is weighed into a stainless steel vessel; Ap01 and methyl paraben are added to it and mixed until dissolved.
b) While stirring is continued, CARBOPOL® homoplymer P is added slowly to Step a) and mixed vigorously at room temperature until a uniform and lump free dispersion is achieved.
c) While stirring is continued, 80% of glycerin is added slowly to Step b) and the contents are mixed contents at room temperature until a uniform dispersion is achieved.
d) While stirring is continued, sufficient pH adjusting agent is added to the mixture to achieve a pH of 5.0 to 6.0.
e) The remaining glycerin is added and mixed until uniform dispersion is achieved.
f) The Dispersion is transferred to a storage vessel and filled.

Example 9: Topical Composition of Apremilast

| Component | % w/w |
| --- | --- |
| Apremilast | 2.00 |
| Dimethyl Sulfoxide | 15.00 |
| CARBOPOL ® homoplymer | 1.20 |
| Glycerin | 79.70 |
| Ethanol | 2.00 |
| Methyl Paraben | 0.10 | a) Approximately 100% of DMSO is weighed into a stainless steel vessel; ethanol and methyl paraben are added and stirred with a propeller mixer.
b) While stirring is continued, Ap01 is added to Step a) and mixed until dissolved.
c) While stirring is continued, CARBOPOL® homopolymer is added slowly to Step b) and mixed vigorously at room temperature until a uniform and lump free dispersion is achieved.
d) While stirring is continued, 80% of glycerin is added slowly to Step c) and the contents are mixed contents at room temperature until a uniform dispersion is achieved.
e) While stirring is continued, sufficient pH adjusting agent is added to the mixture to achieve a pH of 5.0 to 6.0.
f) The remaining glycerin is added and mixed until uniform dispersion is achieved.
g) The Dispersion is transferred to a storage vessel and filled.

Example 10: Pre-Clinical Studies Using Test Formulations

Animal:
The animal model used was Mice (BALB/c,) which were purchased from Mahaveer enterprises and all the experiments were approved by institutional ethical committee.
Protocol:
a) Mice of 8 to 11 wk of age received a daily topical dose of 62.5 mg of commercially available IMQ cream (5%) (Aldara) on the shaved back for 5 or 6 consecutive days; translating to a daily dose of 3.125 mg of the active compound. This dose was empirically determined to cause most optimal and reproducible skin inflammation in mice.
b) Scaling and severity was observed every day
c) To score the severity of inflammation of the back skin, an objective scoring system was developed based on the clinical Psoriasis Area and Severity Index (PASI), except that for the mouse model the affected skin area is not taken into account in the overall score. Erythema, scaling, and thickening were scored independently on a scale from 0 to 5:
0—none;
1—slight;
2—moderate;
3—marked;
4—very marked
5—severe d) The level of erythema was scored using a scoring table with red taints. The cumulative score (erythema plus scaling plus thickening) served as a measure of the severity of inflammation (scale 0-5).
e) The model developed animals were separated into various groups where each group contains three animals.
f) Then various prepared formulations (test with different concentration, 5 mg, 50 mg, and 100 mg of Apremilast) were applied and administered for 5 consecutive days.

Figure 1:
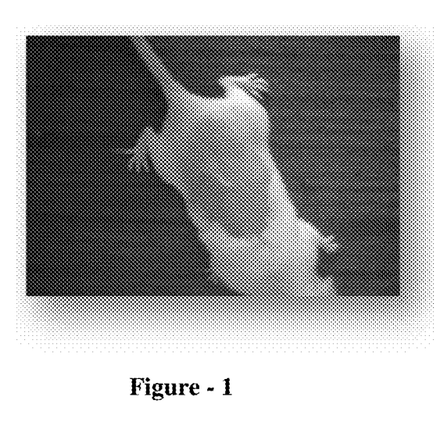
FIG. 1: Shaved control of mice
Figure 2:
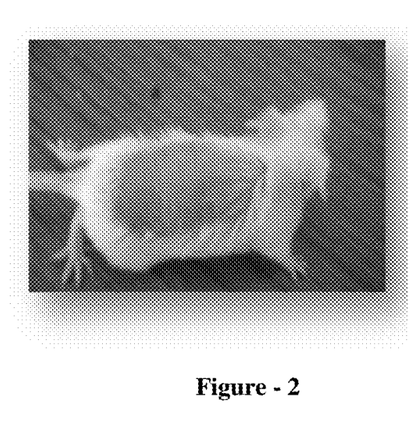
FIG. 2: Imiquamod control
Figure 3:
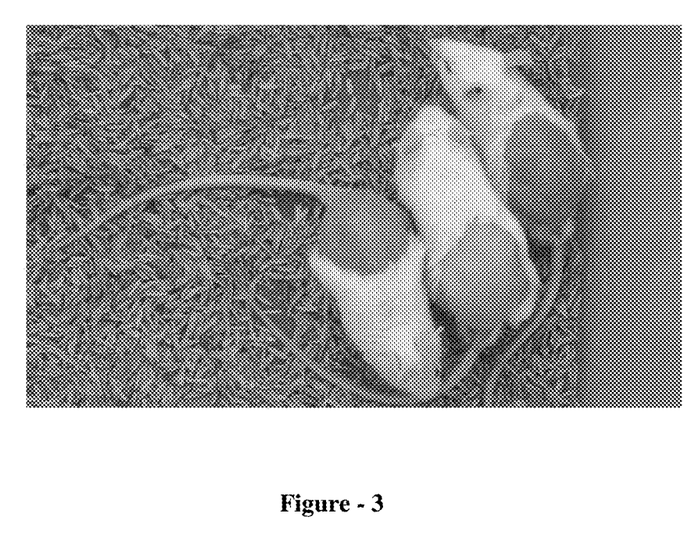
FIG. 3: Mice treated with test product
Figure 4:
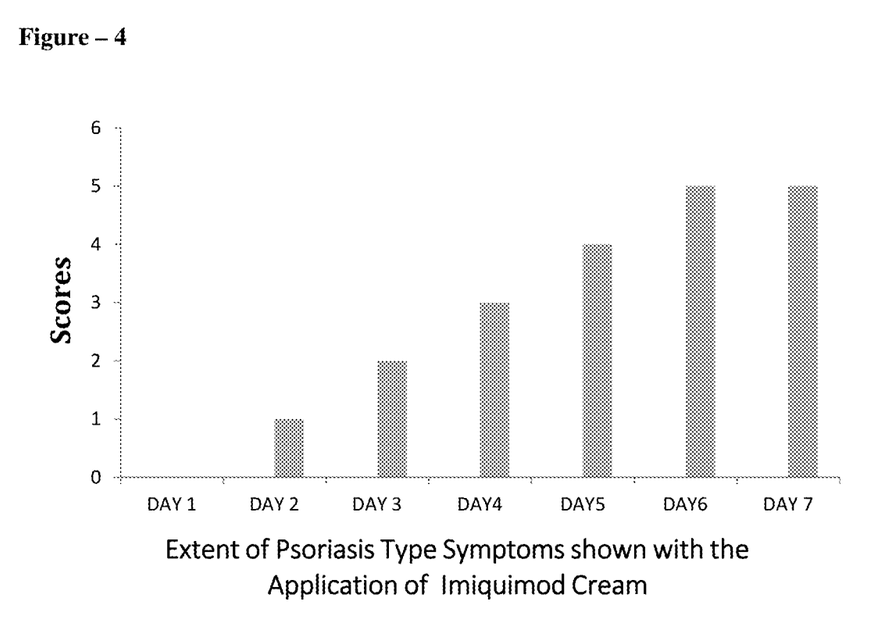
FIG. 4: Graph representing extent of psoriasis symptoms induced after application of imiquamod.
Figure 5:
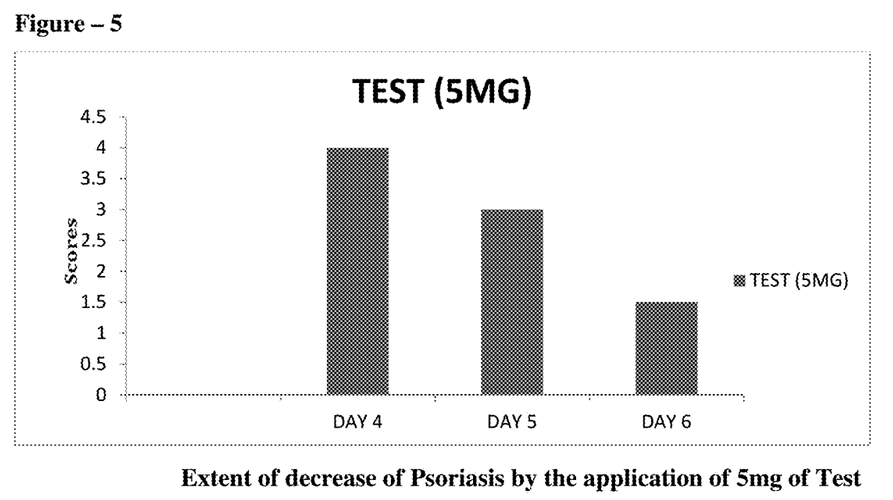
FIG. 5: Graph representing extent of decrease in psoriasis symptoms upon application of 5 mg test
Figure 6:
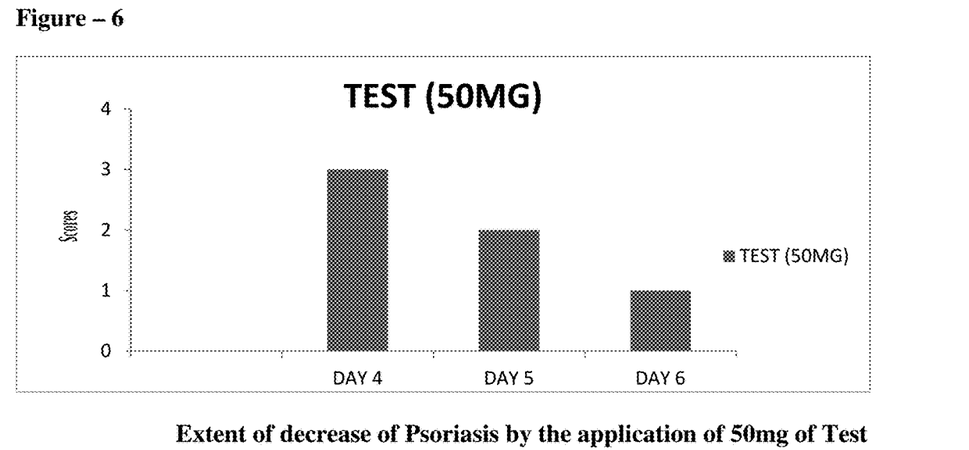
FIG. 6: Graph representing extent of decrease in psoriasis symptoms upon application of 50 mg test
Figure 7:
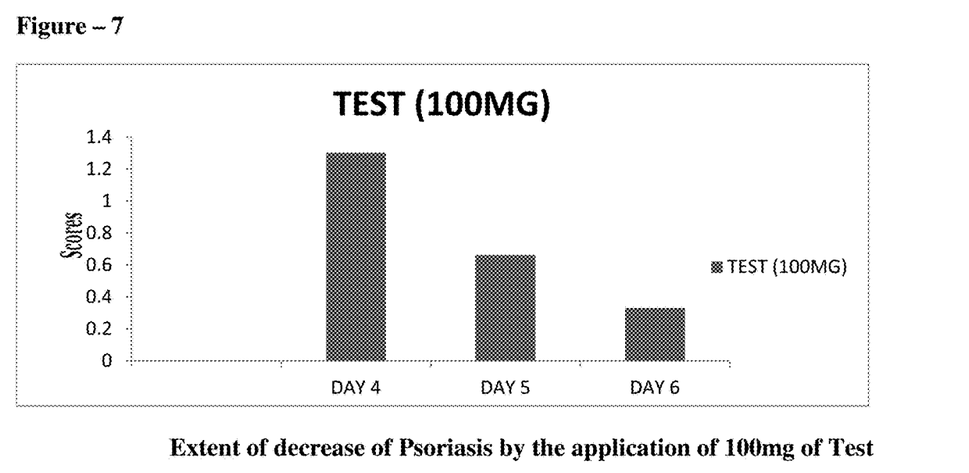
FIG. 7: Graph representing extent of decrease in psoriasis symptoms upon application of 100 mg test
Figure 8:
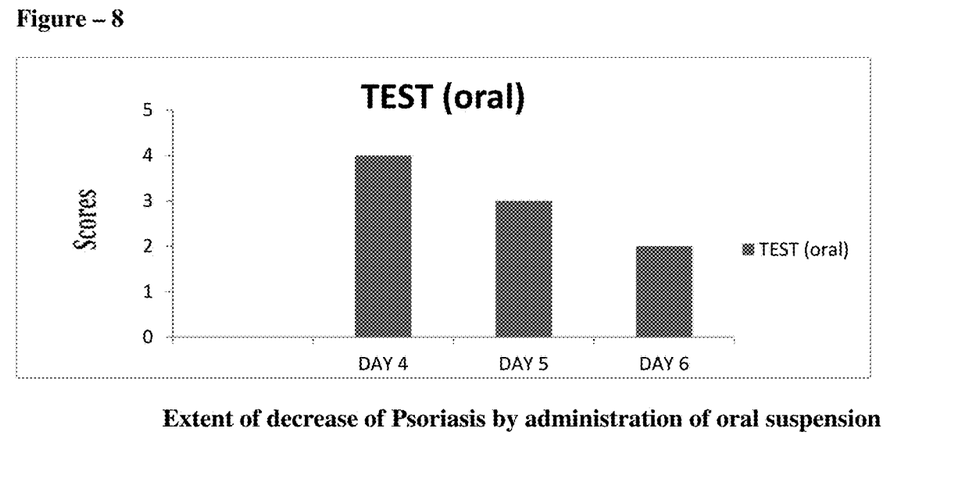
FIG. 8: Graph representing extent of decrease in psoriasis symptoms upon administration of oral suspension

Observations:
a) Two or 3 days after the start of IMQ application, the back skin of the mice started to display signs of erythema, scaling, and thickening. A typical example is shown in FIG. 1
b) The independent scores in a representative experiment are depicted in FIG. 2, wherein from days 2-3 onward inflammation was visible, which continually increased in severity up to the end of the experiment.
c) Mice shaved and treated daily with control cream did not show any sign of inflammation.
d) The scores of individual mice in every group were consistently very similar over a large number of independent experiments, resulting in the typically minimal SDs in FIG. 2.
e) The test formulations showed activity on psoriasis compared to oral suspension (depicted in FIGS. 4, 5, 6, 7 & 8).

Conclusion:
a) All the test formulations showed good results
b) Formulations of 100 mg and 50 mg concentrations have shown better results in reversing the psoriasis type inflammation induced using imiquamod (IMQ cream).

I claim:

1. A topical pharmaceutical composition of apremilast, comprising:
   a. 1-5% w/w of apremilast or pharmaceutically acceptable salt thereof;
   b. a first pharmaceutically acceptable carrier at a concentration range of 5-30% w/w; and
   c. a pharmaceutically acceptable excipient;
   wherein the first pharmaceutically acceptable carrier is selected from the group consisting of dimethyl sulfoxide, glycerol, propylene glycol, petrolatum, water, and a mixture thereof,
   wherein the pH of the said composition is ranging from pH 3 to 8, and
   wherein the said topical composition has the ratio of apremilast to carrier in the range of 1:100 to 100:1.

2. A topical pharmaceutical composition of claim 1, wherein the topical pharmaceutical composition is a cream.

3. A topical pharmaceutical composition of claim 1, wherein the topical pharmaceutical composition is an ointment.

4. A topical pharmaceutical composition of claim 1, wherein the topical pharmaceutical composition is a spray.

5. The topical pharmaceutical composition of claim 1, wherein the pharmaceutically acceptable excipient is selected from the group comprising of skin penetration enhancer, pharmaceutical surfactants, solubility enhancers, oil phase components, aqueous phase components, emulsifiers, anti-oxidants, vitamins, lubricants, preservatives, stabilizers, buffers and mixture thereof.

6. The topical pharmaceutical composition of claim 1, wherein the pH of the composition is maintained in the range from pH 3 to 8 using pH adjusting agents selected from hydrochloric acid, phosphoric acid, lactic acid, diethanolamine, triethanolamine, sodium hydroxide, monobasic sodium phosphate, dibasic sodium phosphate, or a mixture thereof.

7. The topical pharmaceutical composition of claim 1, wherein the pharmaceutically acceptable excipient is a surfactant or emulsifier selected from polysorbate 20, polysorbate 40, polysorbate 60, polysorbate 80, sorbitan ester, sorbitan oleate, sorbitan stearate, polyoxyethylene stearate, sodium lauryl sulphate, stearyl alcohol, poly alkylene glycol ether or a mixture thereof.

8. The topical pharmaceutical composition of claim 1, wherein the carrier in the composition is selected from penetration enhancer, diluent, solubility enhancer, vehicle and a pharmaceutical adjuvant.

9. The topical pharmaceutical composition of claim 1, wherein the said composition is for alleviating or slowing the symptoms of psoriasis within 5 days of administration to a patient that has manifested clinical disease.

10. The topical pharmaceutical composition of claim 1, wherein the said composition comprises of apremilast and dimethyl sulfoxide in a ratio of 1:100 to 100:1.

11. The topical pharmaceutical composition of claim 1, wherein the said composition comprises of apremilast 1-5% w/w, dimethyl sulfoxide, further comprises 20-90% w/w of a second carrier selected from the group consisting of glycerol, propylene glycol, petrolatum, water, and a mixture thereof; and a pharmaceutical excipient selected from skin penetration enhancer, pharmaceutical surfactants, solubility enhancers, oil phase components, aqueous phase components, emulsifiers, anti-oxidants, vitamins, lubricants, preservatives, stabilizers, buffers or mixture thereof, wherein the ratio of apremilast to dimethyl sulfoxide in the composition is ranging between 1:100 to 100:1.

12. The topical pharmaceutical composition of claim 1, further comprising a second pharmaceutically acceptable carrier at a concentration range of 20-90%, wherein the second pharmaceutically acceptable carrier is selected from the group consisting of dimethyl sulfoxide, glycerol, propylene glycol, petrolatum, water, and a mixture thereof.

13. A topical pharmaceutical composition of claim 1, wherein the topical pharmaceutical composition is a gel.

* * * * *